United States Patent [19]

Wallace

[11] Patent Number: 4,658,829
[45] Date of Patent: Apr. 21, 1987

[54] METHOD AND APPARATUS FOR PRESSURE TRANSDUCER CALIBRATION AND SIMULATION

[75] Inventor: William D. Wallace, Salt Lake City, Utah

[73] Assignee: Utah Medical Products, Inc., Salt Lake City, Utah

[21] Appl. No.: 785,966

[22] Filed: Oct. 10, 1985

[51] Int. Cl.$^4$ .............................................. A61B 5/02
[52] U.S. Cl. .................................. 128/672; 128/675; 128/748; 73/4 R
[58] Field of Search .............................. 128/672–673, 128/675, 748; 73/4 R, 708

[56] References Cited

U.S. PATENT DOCUMENTS

| | | | |
|---|---|---|---|
| 3,863,504 | 2/1975 | Borsanyi | 73/395 |
| 4,182,158 | 1/1980 | Culotta et al. | 73/4 R X |
| 4,189,936 | 2/1980 | Ellis | 73/4 R |
| 4,237,900 | 12/1980 | Schulman et al. | 128/673 X |
| 4,339,943 | 7/1982 | Hedrick | 73/4 R |
| 4,342,218 | 8/1982 | Fox | 128/673 X |
| 4,384,470 | 5/1983 | Fiore | 73/4 |
| 4,459,841 | 6/1984 | Hok et al. | 73/4 |
| 4,465,075 | 8/1984 | Swartz | 128/672 |
| 4,556,807 | 12/1985 | Yamada et al. | 73/708 X |
| 4,557,269 | 12/1985 | Reynolds et al. | 128/675 |

FOREIGN PATENT DOCUMENTS 2532761  3/1984  France .................................. 73/4 R

OTHER PUBLICATIONS

Murray et al., "Calib.. System for Catheter Transducer Pressure Measurement"; Biomed. Engr., vol. 11, No. 5, 5-1976, pp. 180–182.
"Veri-Cal Pressure Transducer Tester Instruction Manual," (Utah Medical Products, Inc., Brochure, May 1985).
"Pressure Transducer Simulator," (Brochure for Model BP-28, 5 microvolts/V mmHg, Fogg System Company, Dec. 1983).

Primary Examiner—Kyle L. Howell
Assistant Examiner—Angela D. Sykes
Attorney, Agent, or Firm—Workman, Nydegger & Jensen

[57] ABSTRACT

A method and apparatus for verifying the calibration of a pressure transducer in a pressure monitoring system and for isolating defective electrical components of the monitoring system. The apparatus includes a manually operable pressure cylinder for generating a known test pressure, a pressure calibration circuit coupled to the known test pressure for displaying on the device a calibrated output indicating the level of the known pressure, and a bypass pressure transducer also coupled to the known test pressure for transforming it into an electrical output signal to replace the transducer in the monitoring system as the source of electronically derived readable output in the monitoring system. The substitute pressure transducer includes a temperature compensation circuit and a semiconductor pressure diaphragm with a piezoresistive strain gauge formed thereon. One side of the diaphragm is coupled to the known test pressure and the other side thereof is referenced to atmosphere. The method and device disclosed have particular application in the medical arts to verify the calibration of and test the pressure transducer and cooperating electronic equipment in a direct patient blood pressure monitoring system.

30 Claims, 13 Drawing Figures

PRESSURE / VACUUM  GENERATOR CYLINDER

METHOD AND APPARATUS FOR PRESSURE TRANSDUCER CALIBRATION AND SIMULATION

BACKGROUND OF THE INVENTION

1. Field of the Invention

This invention relates to pressure monitoring systems having an on-line transducer and a monitor for displaying operator readable output electronically derived from the on-line transducer, and more particularly to a method and apparatus for calibration verification of the on-line transducer with a known test pressure, and for selectively bypassing the on-line transducer in order to isolate defective electrical components of the pressure monitoring system.

The method and apparatus of the present invention has particular application to a system for direct monitoring of patient blood pressure and relates in part to subject matter disclosed in my copending U.S. patent application Ser. No. 654,373 for a PRESSURE TRANSDUCER filed on Sept. 25, 1984, and in copending U.S. patent application Ser. No. 608,761 for a DISPOSABLE PRESSURE TRANSDUCER APPARATUS FOR MEDICAL USE filed May 9, 1984, which are both incorporated herein by reference.

2. Background Art

The continuous monitoring of the pressure in a given environment is of importance in many aspects of manufacturing, transportation, health care, and energy production. Increasingly, pressure monitoring systems in these areas are of an electronic nature, utilizing a pressure transducer to convert the pressure in the environment monitored into an electrical signal reflective of the level thereof for display on a monitor.

For example, in medical science when monitoring direct patient blood pressure, it is known to couple a pressure transducer to a sterile fluid contained in a catheter inserted into a circulatory vessel of a patient. As the heart beats, the blood pressure waves are transmitted through the fluid in the catheter to the transducer, which produces an electrical output readable in digital or analog fashion on an electronic monitor. Advances in this area have produced miniature, yet sturdy, pressure transducers which are economical enough so as to be disposable after use with only a single individual patient.

With respect to pressure monitoring systems for use in this and other fields in which electronic pressure monitoring systems are significant, there is an important need to verify the accuracy of the monitoring system, both upon initial implacement and on a continuous basis during operation. The function of verifying an electronic pressure monitoring system involves two aspects.

First, the on-line pressure transducer of such a system must be tested through application thereto of a known test pressure to determine whether the transducer and its cooperating electronic equipment are functioning correctly together to read pressures monitored by the system. Calibration verification of the system against the known test pressure is thus one objective.

If, however, testing of the transducer and its cooperating electronic equipment reveals a malfunction in the monitoring system, a second aspect of verification requires that the source of the malfunction be isolated and then corrected. Typically, in order to accomplish this, electronic equipment has been required in addition to that used to check calibration of the on-line transducer. This additional electronic equipment simulates the electrical output behavior of the on-line transducer of the system and is connected to the system in place thereof, replacing it as the source of electrical signals to the monitoring system.

If this additional electronic equipment and procedure continues to reveal malfunctioning, then it can be assumed that the source of the malfunction resides, not in the on-line transducer, but in the electronic monitor or connecting cable of the monitoring system, although it is possible that both components and even the on-line transducer are each malfunctioning independently of the others. This knowledge then permits isolation of the defective electrical component, usually through interchanging one or the other of the monitor or cable used in the electronic system. On the other hand, if no malfunctioning of the electronic equipment of the system is manifested by this procedure, then the source of malfunction can be concluded to reside with the on-line transducer of the system. Understanding the location of any malfunction then permits its correction, usually by replacement of an appropriate component of the system.

Transducer simulators have in the past been devices which use complex resistive network circuitry to produce discrete levels of electronic signals imitating a transducer output through switching among an array of electronic components. These devices do not produce output signals within a continuous range of values, and in fact do not always reliably replicate the response of a transducer to a source of pressure within the range expected to be monitored.

Further, such transducer simulators, by not including transducers like those in place of which they are used, do not include the precise capacitive and inductive impedances thereof. They cannot, therefore, be expected to effectively simulate the interreaction of the transducer they replace with the monitor of the system being tested. This problem is only further compounded by the wide variety of monitors in use.

SUMMARY OF THE INVENTION

It is desirable that equipment for performing the two aspects of verification be inexpensive, simple in operation, and highly portable. Additionally, as the tasks of testing a transducer within its monitoring system and isolating any malfunction are so closely related, it is desirable to have the equipment for performing both functions available in a single unit. It is further desirable that the transducer simulator portion of such equipment be of an analog nature, including a transducer which, in the optimal situation would be similar in character to the transducer of the system being tested.

Consistent with the foregoing, one object of the present invention is to produce a method and apparatus for use therein which is at once capable of both verifying the calibration of an on-line transducer within a pressure monitoring system using a known test pressure and, by using a second transducer having electrical characteristics which very closely replicate those of the on-line transducer, selectively replacing the on-line transducer in the system when there is a need to locate defective electrical components therein.

Another object is to provide an apparatus for use in such a method which is sufficiently compact as to be held in the hand of an operator of the monitoring system.

Still another object of the present invention is to provide a device capable of bypassing the on-line transducer in a pressure monitoring system by using a bypass transducer that is capable of producing a continuous range of output virtually identical to that of the bypassed on-line transducer, the bypass transducer deriving its own output signal responsive to the application of a known test pressure.

Yet another object is to provide a method and apparatus which is readily connectable to the monitoring system being tested, which results in minimal difficulty to use even by unsophisticated personnel, and which is inexpensive to manufacture.

The foregoing and other objects and advantages of the invention are realized and obtained by means of the method and apparatus of the present invention. In one presently preferred embodiment of the invention, a small, hand-held device includes a manually operable pressure cylinder for generating a known test pressure. The known test pressure is applied to a pressure calibration circuit which derives and displays in operator readable form a calibrated output indicating the level of the known test pressure. The known test pressure is also applied to the on-line transducer of a pressure monitoring system so that the on-line transducer also derives an operator readable output that is displayed on the monitor of the pressure monitoring system. The output of the monitor can then be compared to the calibrated output indicated on the device. If the output on the monitor and the calibrated output are different, the on-line pressure transducer can then be unplugged from the monitor and connecting cable of the pressure monitoring circuit, which are then connected into a substitute pressure transducer provided in the device. The known test pressure is also applied to the substitute pressure transducer, which is powered from the monitor to which it is connected for testing, and the substitute pressure transducer then derives an operator readable output which is displayed on the monitor. If the output on the monitor and the calibrated output on the device are the same, the user then knows that the on-line transducer is defective and can replace it. If the output on the monitor and the calibrated output on the device continue to be different, the user then knows that either the connecting cable or the monitor is defective, and therefore can further isolate and then replace the defective component of the system.

BRIEF DESCRIPTION OF THE DRAWINGS

The invention will be more fully understood from a detailed description of the drawings, in which like parts are designated with like numerals throughout, and in which.

DESCRIPTION OF THE PREFERRED EMBODIMENT

Figure 1:
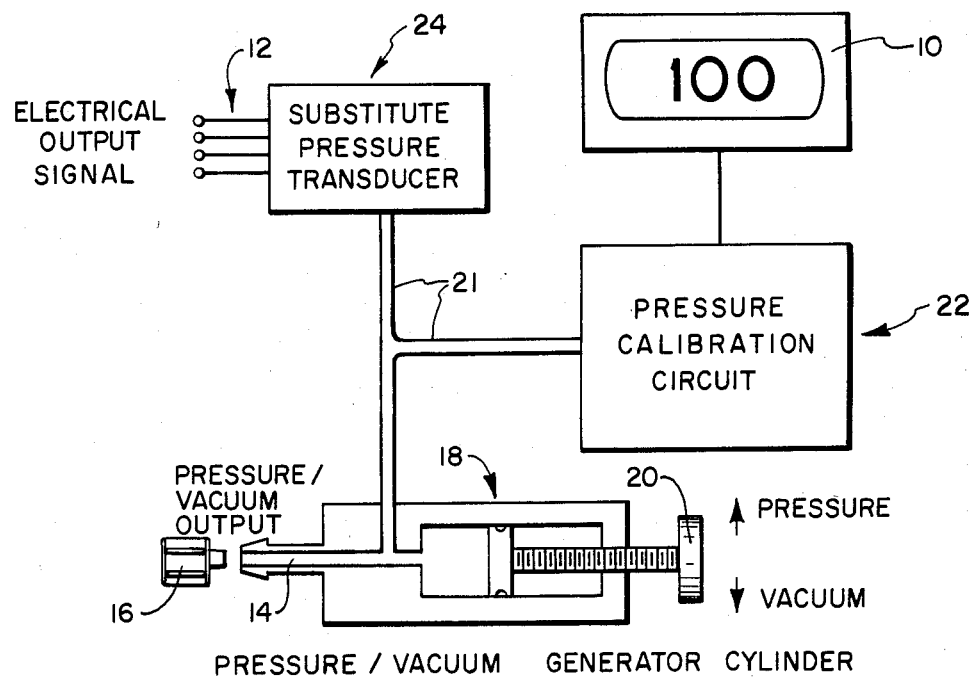
FIG. 1 is a schematic diagram illustrative of the method and apparatus of the present invention.

A helpful overview of the method and apparatus of the present invention, which are for use with a pressure monitoring system having an on-line pressure transducer and a monitor for displaying operator readable output electronically derived from the on-line pressure transducer, can be obtained by reference first to FIG. 1. Therein it is shown that a device according to the present invention includes a display panel meter 10 and two outputs, namely an electrical output signal appearing at an electrical receptacle 12 and pressure or vacuum output produced at an output port 14. Output port 14 is selectively closeable according to the needs of is operator, as is suggested by a cap 16 therefor. Nevertheless, any means for selectively opening and closing output port 14, such as a valve integral therewith or a hose connected thereto incorporating a stopcock, is entirely appropriate in this regard.

In accordance with the present invention operator variable means is provided for generating a known test pressure at output port 14. Shown in FIG. 1, by way of illustration and not limitation, a manually operable pressure cylinder 18, including rotatable adjustment knob 20, is connected to output port 14. Depending on the direction of rotation of adjustment knob 20, a pressure or a vacuum can be made to appear at output port 14. Accordingly, it should be understood that the term "known test pressure" as used hereafter refers to a range of values including either or both positive and negative pressures.

The known test pressure generated by pressure cylinder 18 is applied simultaneously through pneumatic lines 21 to a pressure calibration circuit 22 and to a substitute pressure transducer 24. Pressure calibration circuit 22 and display panel meter 10 to which it is electrically connected together typify a pressure calibration means provided for displaying on a device of the present invention a calibrated output indicating the level of the known test pressure generated in pressure cylinder 18, as indicated by the number 100 appearing on the display panel meter 10. Substitute pressure transducer 24 transforms the known test pressure generated in pressure cylinder 18 to an electrical output signal at electrical receptacle 12 corresponding to the level of the known test pressure generated in cylinder 18 and being of the same type as the electrical signal derived from the on-line pressure transducer in the monitoring system with which the device of the present invention is utilized, as hereinafter more fully explained.

To calibrate the pressure monitoring system, the known test pressure generated in pressure cylinder 18 is coupled to the on-line pressure transducer in that system in order to produce on the monitor thereof a first operator readable output which reflects the direct responsiveness to the known test pressure of the monitoring system, including the on-line pressure transducer. Thereafter, by checking the first operator readable output on the monitor against the calibrated output on display panel meter 10 of the device, the monitoring system may be accurately calibrated. If calibration cannot be achieved, then it may be concluded that some component of the monitoring system is malfunctioning.

In such case, it will be further necessary to locate and eliminate the malfunction, an objective in which a device according to the present invention also has utility. The output signal of substitute pressure transducer 24 is used to replace the on-line pressure transducer of the pressure monitoring system as a source of operator readable output to that system. This is accomplished by connecting the electrical output signal appearing at electrical receptacle 12 to selected locations in the monitoring system. At each location, the electrical output signal from electrical receptacle 12 produces on the monitor of the pressure monitoring system a second operator readable output which can be checked against the output on display panel meter 10 of the device in order to isolate defective electrical components in the pressure monitoring system. In this light, substitute pressure transducer 24, shown in FIG. 1, is illustrative of a bypass means for transforming the known test pressure generated in pressure cylinder 18 into an electrical output signal of the type derived from the on-line pressure transducer in the monitoring system, and electrical receptacle 12 connected thereto functions as a second output means couplable by the operator to selected locations in the monitoring system to electrically bypass the on-line pressure transducer thereof.

In the process of bypassing the on-line transducer to isolate defective electrical components, the coupling of output port 14 to the pressure monitoring system can be maintained if permitted by the physical dimensions of the pressure monitoring system and the connectors being utilized to couple the device of the present invention. If it is necessary to uncouple output port 14, however, or if the process of connecting electrical receptacle 12 to the pressure monitoring system results in venting the known test pressure at output port 14 through components of the pressure monitoring system, then output port 14 should be closed, by a cap, such as cap 16, or any equivalent thereof. In this manner output port 14 functions as a closeable first output means selectively couplable by the operator to the pressure monitoring system for applying the known test pressure generated by pressure cylinder 18 to the on-line pressure transducer of the pressure monitoring system.

The method and apparatus of the present invention will now be described in detail and with specific reference to its use in connection with a direct patient blood pressure monitoring system having an on-line pressure transducer coupled through a fluid in a catheter inserted into a circulatory vessel of a patient, the system also having a monitor for displaying an operator readable output electronically derived from the on-line pressure transducer.

Figure 2:
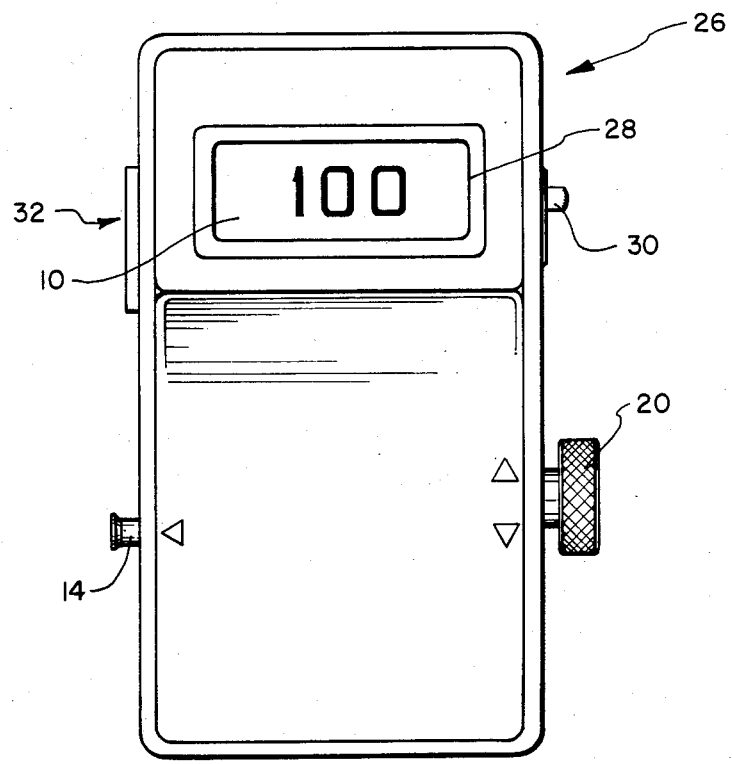
FIG. 2 is a plan view of the exterior of a device embodying the present invention.

An example of such a device, and one further dimensioned so as to be held in the hand of an operator, is shown in its external aspects of FIG. 2 as device 26. In the upper surface of device 26 is formed a window opening 28 through which may be viewed display panel meter 10. A pressure cylinder adjustment knob, such as adjustment knob 20, projects from a side of device 26 opposite from a pressure/vacuum output port, such as output port 14. Device 26 is further equipped with an electrical switch 30 and an electrical connector 32.

Figure 3:
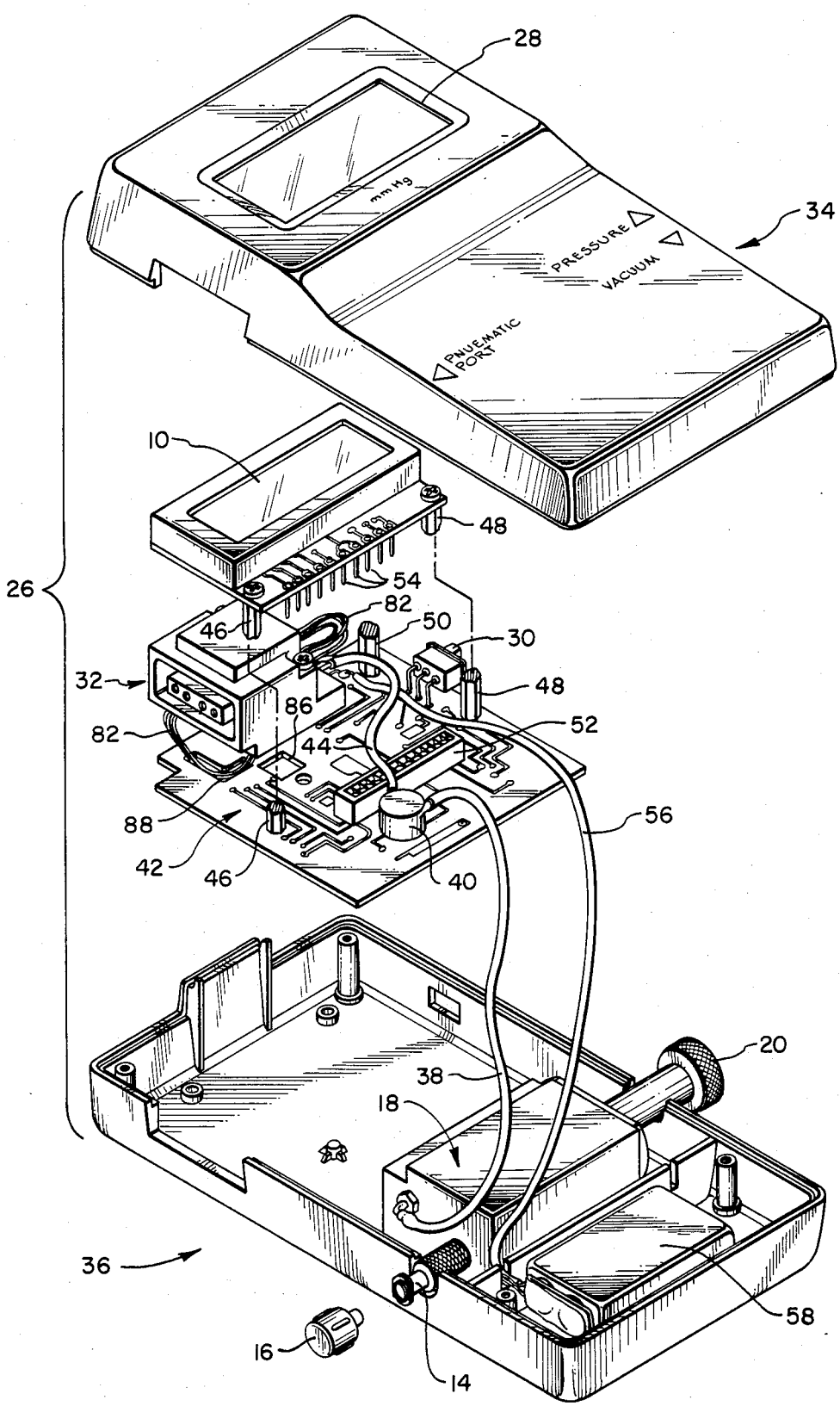
FIG. 3 is an exploded perspective view of the device of FIG. 2.

Referring to FIG. 3, device 26 can be seen to include a number of components housed within a case consisting of an upper housing 34 and a lower housing 36. As illustrated, these components include a suitable pressure cylinder 18 operator variable through use of adjustment knob 20 and having an output port 14 formed as a conventional luer fitting. Pressure cylinder 18 is coupled pneumatically through tubing 38 to a cap 40 covering a precision pressure transducer mounted on a printed circuit board 42. Cap 40 functions in addition as an uninterrupted pneumatic coupling between tubing 38 and additional tubing 44 which communicates through an electrical connector 32 to a substitute pressure transducer mounted on the underside thereof in a manner to be explained in detail hereafter. Display panel meter 10 is supported on posts 46, 48, 50 above printed circuit board 42 and connected electrically to the circuitry thereon through the cooperating action of receptacle 52 mounted on printed circuit board 42 and pins 54 of display panel 10. All circuitry in the device with the exception of that included within the substitute pressure transducer on the underside of electrical connector 32 is powered through an electrical lead 56 from a battery 58 contained within device 26.

Figure 4:
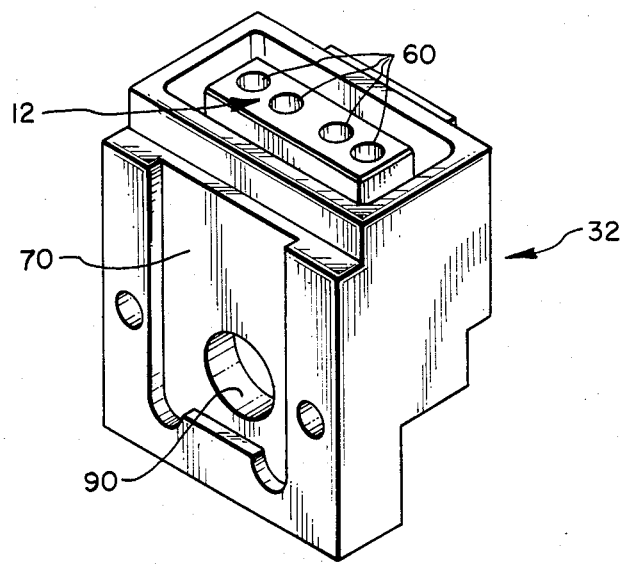
FIG. 4 is a perspective view of the bottom and two sides of a connector and substitute pressure transducer mount for the device of FIG. 2.
Figure 5:
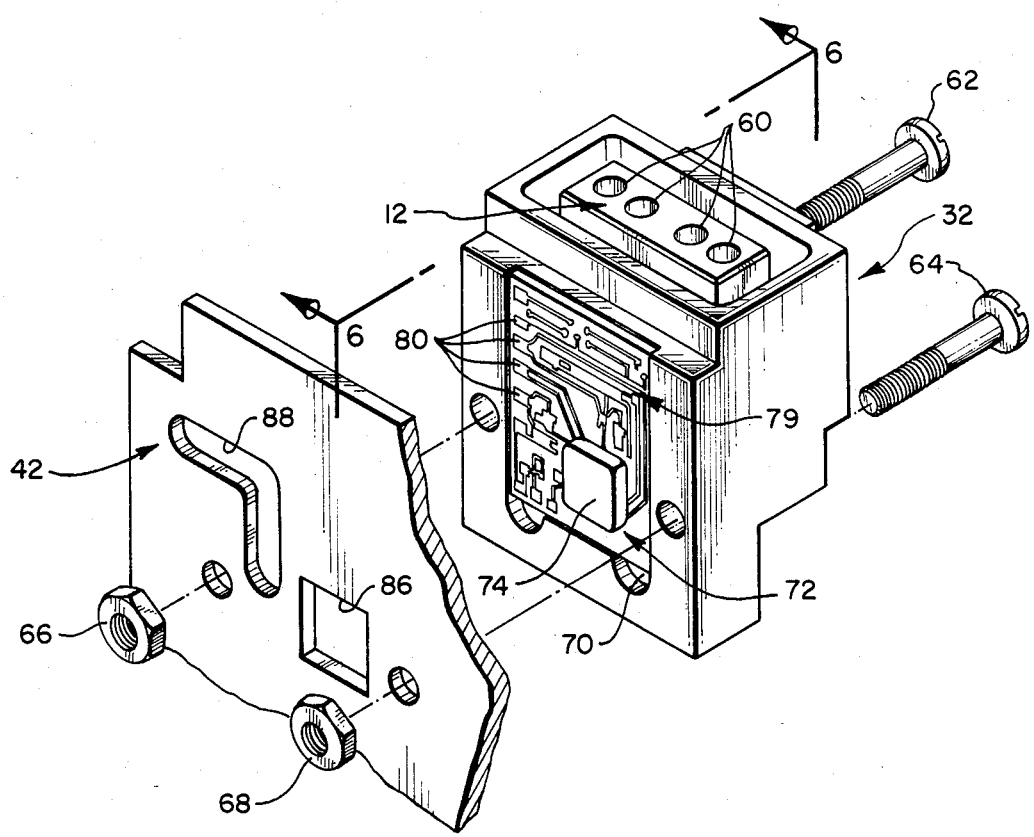
FIG. 5 is an exploded perspective view of the connector of FIG. 4 shown in relation to other elements of the device in FIG. 2 to which it is assembled.

Referring to FIGS. 4 and 5 together, electrical connector 32 can be seen to include an electrical receptacle 12 which includes a number of electrical contact receiving bores 60. On the underside of electrical connector 32, facing printed circuit board 42 to which it is secured by screws 62, 64 and nuts 66, 68 respectively, electrical connector 32 is provided with a recess 70 for receiving a dielectric substrate 72 which may be formed of any of a number of suitable dielectric materials, as for example, a ceramic material.

Figure 6:
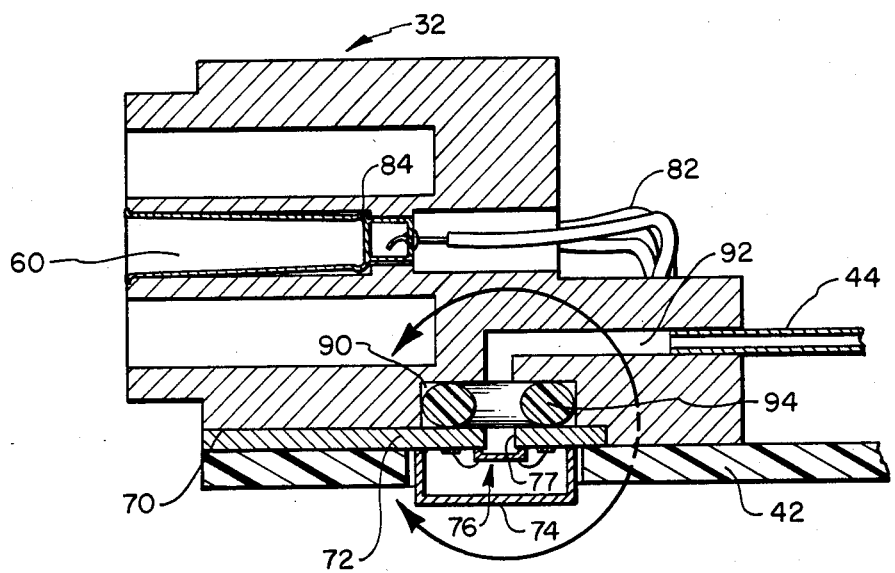
FIG. 6 is a cross-sectional view of the device shown in FIG. 5 taken along section lines 6—6.
Figure 7:
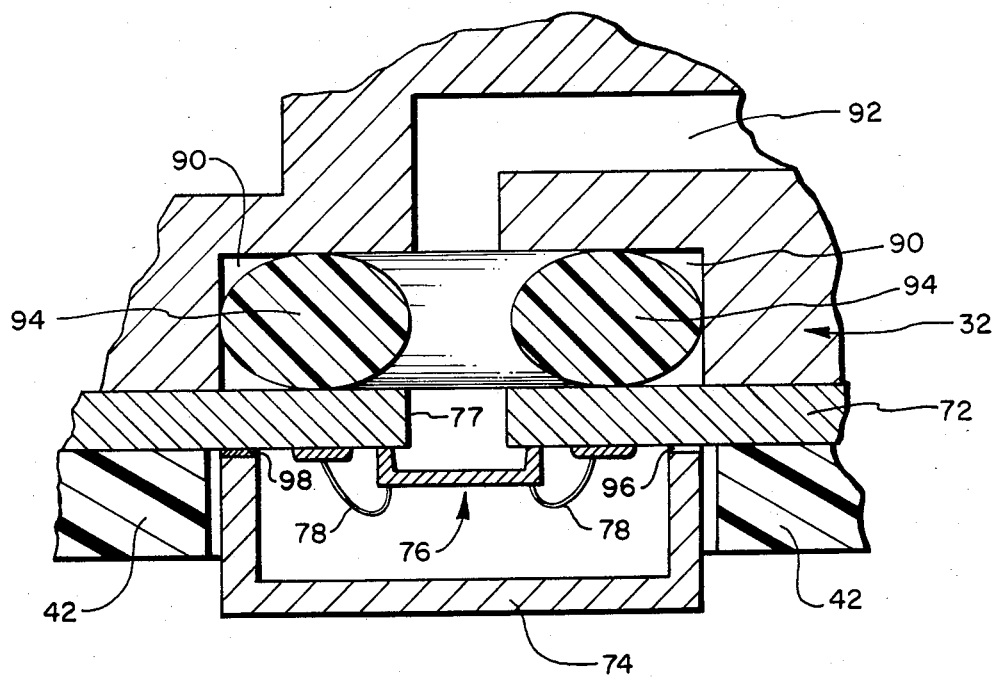
FIG. 7 is an enlarged cross-sectional detail of one aspect of the device shown in FIG. 6.

Referring in addition to FIGS. 6 and 7, from the side of dielectric substrate 72 facing printed circuit board 42 projects a cover 74 covering a semiconductor pressure diaphragm 76 sealed at the periphery thereof over an aperture 77 formed in dielectric substrate 72. On the side of semiconductor pressure diaphragm 76 opposite from aperture 77 is formed a piezoresistive strain gauge (not shown), which is connected to other circuitry on the same side of dielectric substrate 72 through leads 78.

As schematically shown in FIG. 5, dielectric substrate 72 is further provided on the side thereof facing printed circuit board 42 with a conventional temperature and gain compensation circuit 79 which is used to adjust both the zero pressure point and the gain of the strain gauge associated with semiconductor pressure diaphragm 76, such that these parameters will not change with variations in temperature. Temperature and gain compensation circuit 79 also determines the gain or sensitivity of the strain gauge on semiconductor pressure diaphragm 76, such gain being typically on the order of 5 microvolts of signal per volt of excitation per millimeter of mercury pressure. Further, temperature and gain compensation circuit 79 is used to match the input and output impedance of the strain gauge on semiconductor pressure diaphragm 76 with that of the on-line pressure transducer which is to be bypassed in the pressure monitoring system. This provides a substitute for the on-line pressure transducer which has electrical characteristics, such as signal strength, inductive, capacitive, and resistive impedances, and response time, identical or very similar to those of the on-line pressure transducer. Temperature and gain compensation circuit 79 may be provided on dielectric substrate 72 in any suitable manner, as for example, by using appropriate silk screening techniques. Thereafter, the various components of temperature compensation circuit 79 may be laser trimmed to the required values by means which are known in the art.

Dielectric substrate 72 is further provided with solder pads 80 electrically connected to temperature and gain compensation circuit 79 and through electrical wires 82 (see FIGS. 3 and 6) to metal sleeves 84 within each of electrical contact receiving bores 60. Dielectric substrate 72 is held in recess 70 by the pressure of printed circuit board 42 when electrical connector 32 is attached thereto. Accordingly, in order to accommodate for cover 74, an opening 86 is provided at a corresponding location in printed circuit board 42. In similar fashion an L-shaped opening 88 is formed in printed circuit board 42 to facilitate routing of electrical wires 82 from the back of connector 32 to solder pads 80. (See also FIG. 3.)

Referring now to FIGS. 6 and 7, the coupling of the known test pressure generated in pressure cylinder 18 to the bypass means of the present invention will be illustrated. In recess 70 of electrical connector 32 there is formed a cylndrical recess 90 which communicates through a passageway 92 formed in electrical connector 32. Passageway 92 is connected to additional tubing 44, and thus to the known test pressure generated at pressure cylinder 18. An O-ring 94 housed within cylindrical recess 90 is compressed by dielectric substrate 72, when electrical connector 32 is assembled to circuit board 42, producing an air tight seal between passageway 92 and aperture 77 in dielectric substrate 72.

The known test pressure generated in pressure cylinder 18 thus impacts upon semiconductor pressure diaphragm 76 through aperture 77 of substrate 72. The piezoresistive strain gauge formed on the opposite side of diaphragm 76, in combination with temperature and gain compensation circuit 79, produces in a known manner electrical output signals corresponding to the level of the known test pressure. The side of semiconductor pressure diaphragm 76 on which is formed the piezoresistive strain gauge is referenced to atmospheric pressure through the provision of a vent in cover 74, such as opening 96 in an adhesive 98 with which cover 74 is attached to dielectric substrate 72.

Figure 8:
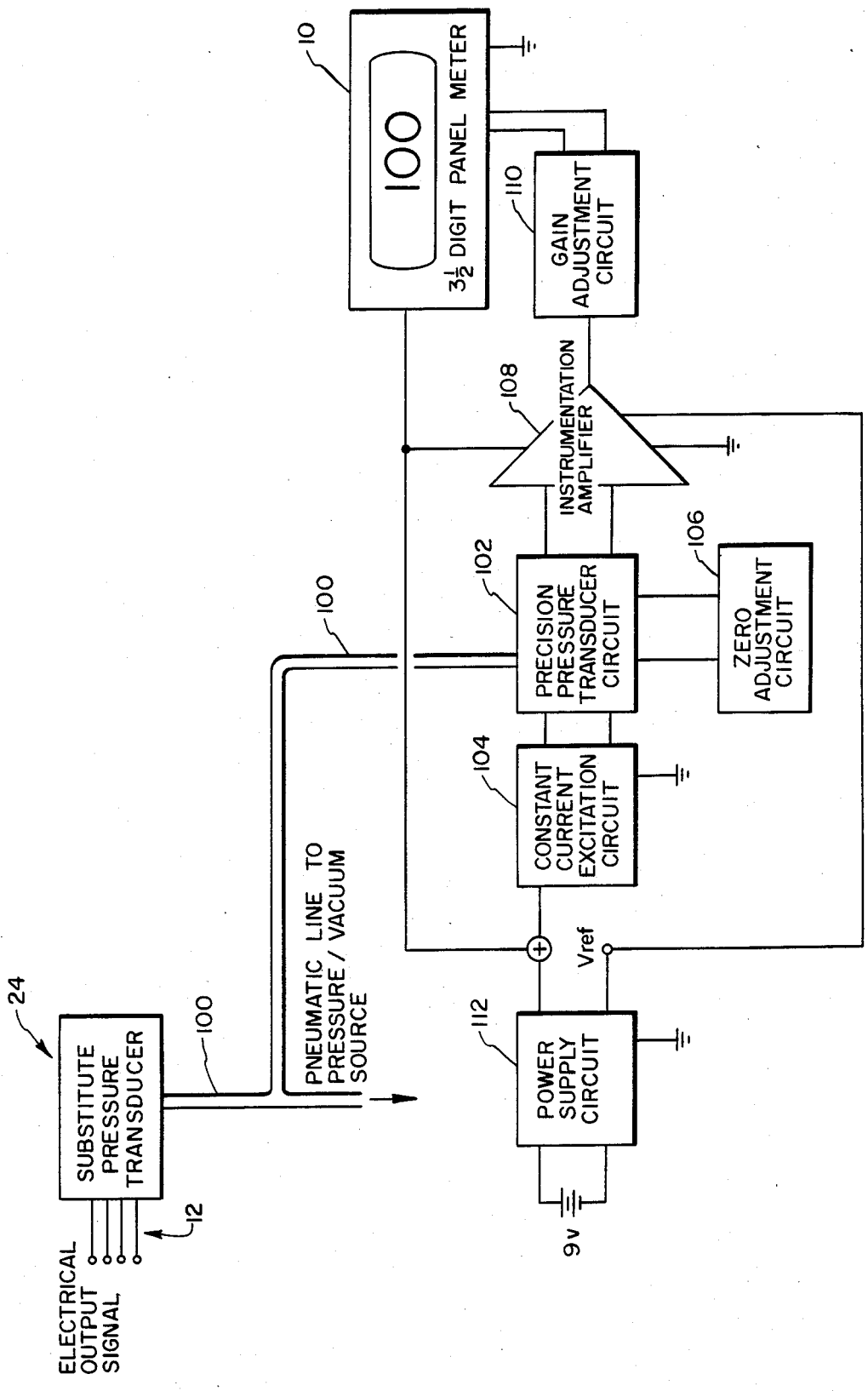
FIG. 8 is a functional schematic diagram of the pressure calibration circuit and substitute transducer employed in the device shown in FIG. 2.

In accordance with the present invention pressure calibration means are provided for displaying on the device of the present invention a calibrated output indicating the level of the known test pressure generated in pressure cylinder 18. As shown schematically in FIG. 8, the known test pressure is applied through pneumatic lines 100 to a precision pressure transducer circuit 102 which is provided through a constant current excitation circuit 104 with one milliampere of constant excitation current. Precision pressure transducer circuit 102 is calibrated for zero pressure using a zero adjustment circuit 106, and the output of precision pressure transducer circuit 102 is communicated through an instrumentation amplifier 108 to a gain adjustment circuit 110 for display on display panel meter 10. In this embodiment of the invention display panel meter 10 is a 3½ digit panel meter Model No. BL 176 from Modutec. Power to this circuitry is provided through a power supply circuit 112 using a 9 volt direct currrnt source, such as battery 58 shown in FIG. 3. All the elements 102-112 shown in FIG. 8 are included on printed circuit board 42 shown in FIG. 3. Power to substitute pressure transducer 24 is provided through electrical receptacle 12 from the pressure monitoring system to which the device of the present invention is connected for testing.

Figure 9:
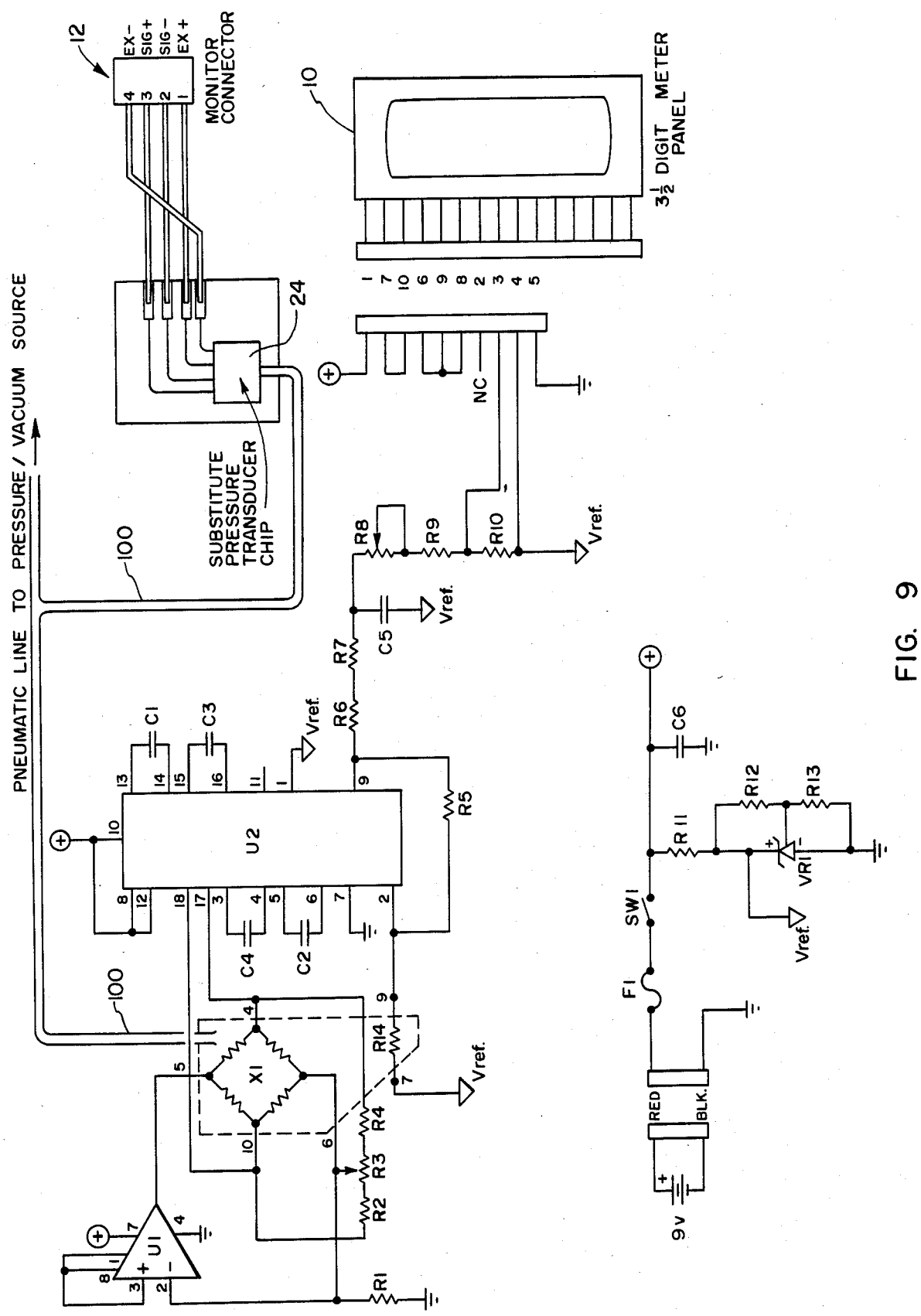
FIG. 9 is a detailed electrical schematic diagram of a preferred embodiment capable of implementing the functions illustrated in FIG. 8.

A more detailed description of a preferred embodiment showing circuitry capable of performing the functions illustrated in FIG. 8 can be found in FIG. 9, wherein U1 is an LM10 operational amplifier with a built-in voltage reference, and U2 is an ICL7605 instrumentation amplifier by Intersil. A preferred precision pressure transducer X1, Model 9049-5 from IC Sensor, is coupled to the test pressure generated in pressure cylinder 18 through pneumatic lines 100, which also communicate with substitute pressure transducer 24. VR1 is an LM385Z voltage regulator; and F1 is a quarter ampere fast-blow fuse. SW1 corresponds to electrical switch 30 shown in FIGS. 2 and 3. Components U1, U2, X1 and display panel meter 10 are each connected at the numbered pins thereof as shown.

In FIG. 9 component F1, SW1, VR1, R11, R12, R13, and C6 function as power supply circuit 112 shown in FIG. 8. Operational amplifier U1 in combination with R1 function as constant current excitation circuit 104. The zero adjustment circuit 106 consists of resistors R2 and R4 in combination with adjustable resistor R3. Series-connected resistors R6 and R7 in combination with C5 function as a 1.5 Hz low pass fillter within instrumentation amplifier 108. Instrumentation amplifier 108 further includes U2, C1, C2, C3, C4, R5 and R14, a laser trimmed again resistor contained within the X1 package. Resistors R9 and R10 and adjustable resistor R8 together function as gain adjustment circuit 110. Values of all components are listed in Table I below:

TABLE I

| Resistors | |
|---|---|
| R1 = 200 Ω | R8 = 100k Ω |
| R2 = 500k Ω | R9 = 100k Ω |
| R3 = 100k Ω | R10 = 29.4k Ω |
| R4 = 500k Ω | R11 = 100k Ω |
| R5 = 100k Ω | R12 = 100k Ω |
| R6 = 500k Ω | R13 = 182k Ω |
| R7 = 500k Ω | |

| Capacitors | |
|---|---|
| C1 = 1.0 μf | C4 = 1.0 μf |
| C2 = 1.0 μf | C5 = 0.1 μf |
| C3 = 1.0 μf | C6 = 0.1 μf |

Figure 10:
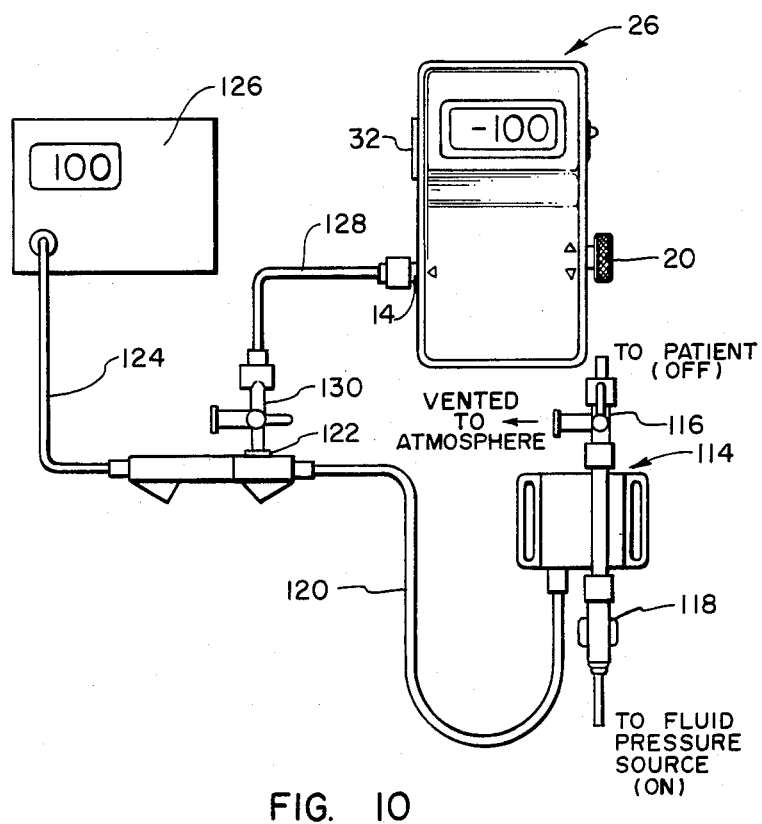
FIG. 10 is a diagram illustrating the use of the device of FIG. 2 to verify the calibration of an on-line transducer in a direct blood pressure monitoring system to a known test pressure.
Figure 11:
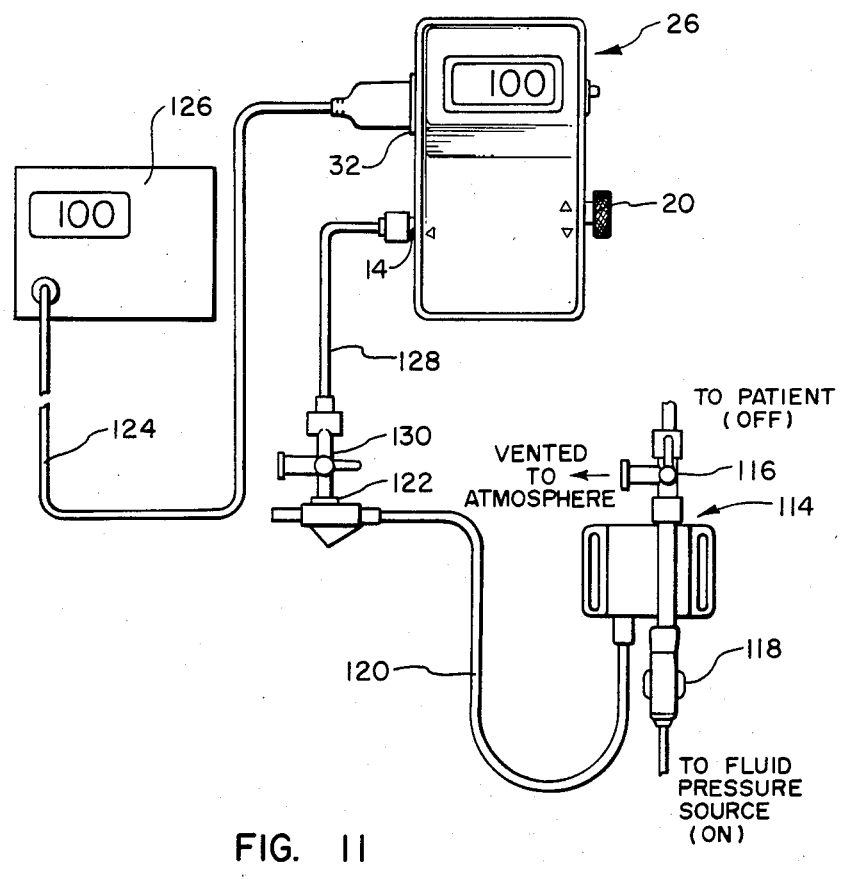
FIG. 11 is a diagram illustrating the use of the device shown in FIG. 2 to bypass the on-line transducer of the system when isolating a defective component.

The operational use of a device according to the present invention, such as device 26 depicted herein, will be explained in relation to two types of direct blood pressure monitoring systems. First, FIGS. 10 and 11 illustrate use of device 26 to verify the calibration of an on-line disposable pressure transducer 114, such as is described in copending U.S. patent application Ser. No. 608,761, and to bypass on-line disposable pressure transducer 114. In a preferred embodiment of device 26 of the present invention, substitute pressure transducer 24 is substantially identical to disposable pressure transducer 114. Disposable pressure transducer 114 is normally coupled through a stopcock 116 to a fluid filled catheter inserted within a circulatory vessel of a patient. The coupling fluid is provided through a known continuous flush device 118 from a source of fluid under pressure. Disposable pressure transducer 114 is referenced at one side of the transducer diaphragm thereof to atmosphere through a cable 120 having an atmospheric vent 122 thereon. The other side of the diaphragm of transducer 114 is coupled through a hydraulic gel with the fluid in the catheter. Cable 120 communicates an electrically derived output from disposable pressure transducer 114 through a second cable 124 to monitor 126, where a pressure level is displayed.

To use device 26 in order to verify the calibration of disposable pressure transducer 114, output port 14 of device 26 is connected by some suitable tubing, such as a hose 128 to vent 122. Using adjustment knob 20, a negative pressure is generated in device 26, as exemplified by the negative 100 mmHg appearing on the face thereof in FIG. 10. This pressure is communicated through hose 128 and the vent 122 provided with electrical cable 120 to the nonsterile side of disposable pressure transducer 114, which is otherwise referenced to atmospheric pressure. Transducer 114 is accordingly stimulated to respond electrically as if a corresponding positive pressure were applied on the sterile or patient side thereof. The output electronically derived from disposable pressure transducer 114 is input to monitor 126 through cable 120 and a second cable 124 and can be checked against that appearing on the face of device 26. Hose 128 can optionally be provided with a cutoff valve, such as stopcock 130. During the verification of the calibration of disposable pressure transducer 114, another valve, such as stopcock 116, is turned off in the direction of the patient and opened to the atmosphere to vent the patient side of disposable pressure transducer 114. As shown in FIG. 10, a reading of 100 mmHg on monitor 126 in response to a reading of negative 100 mmHg on device 26 indicates that disposable pressure transducer 114, cable 120, second cable 124, and monitor 126 are calibrated.

If calibration of disposable pressure transducer 114 cannot be verified, it is necessary to locate the source of the malfunctioning. This is accomplished, as shown in FIG. 11, by connecting the output signal of the substitute transducer of device 26, which appears at electrical connecter 32, to selected locations in the monitoring system in order to replace disposable pressure transducer 114 as the source of operator readable output to monitor 126. This is illustrated in FIG. 11, in which the cable 124 from monitor 126 has been disconnected from electrical cable 120 and inserted directly into electrical connector 32 in device 26. This results in bypassing transducer 114 in order to test whether the second cable 124 and monitor 126 function correctly when disposable pressure transducer 114 and electrical cable 120 are removed and substitute pressure transducer 24 of device 26 is substituted therefor. In this test, as depicted in FIG. 11, adjustment knob 20 has been used to generate a pressure on device 26 corresponding to 100 mmHg, which is reflected in an equal reading on the face of monitor 126. This result suggests that any problem in the monitoring system would be located in disposable pressure transducer 114 or cable 120 connected thereto.

Were the reading on monitor 126 at variance with that on device 26, it could be concluded that malfunctioning in the system was from a defect in monitor 126 or second cable 124. A determination as to which of these two devices was defective could be obtained, for example, through connecting monitor 126 to electrical connector 32 of device 26 with a cable known to be good, thereby eliminating the effects of second cable 124 from the system.

It should be noted that in checking the pressure monitoring system for defective electrical components in this manner, the pressure generated in device 26 at output port 14 cannot be permitted to vent to atmosphere. Accordingly, it may be necessary, for example, to close off valve 130, if tubing 128 is disconnected from vent 122 on cable 120, or to seal output port 14 with cap 16, if tubing 128 is disconnected therefrom.

Figure 12:
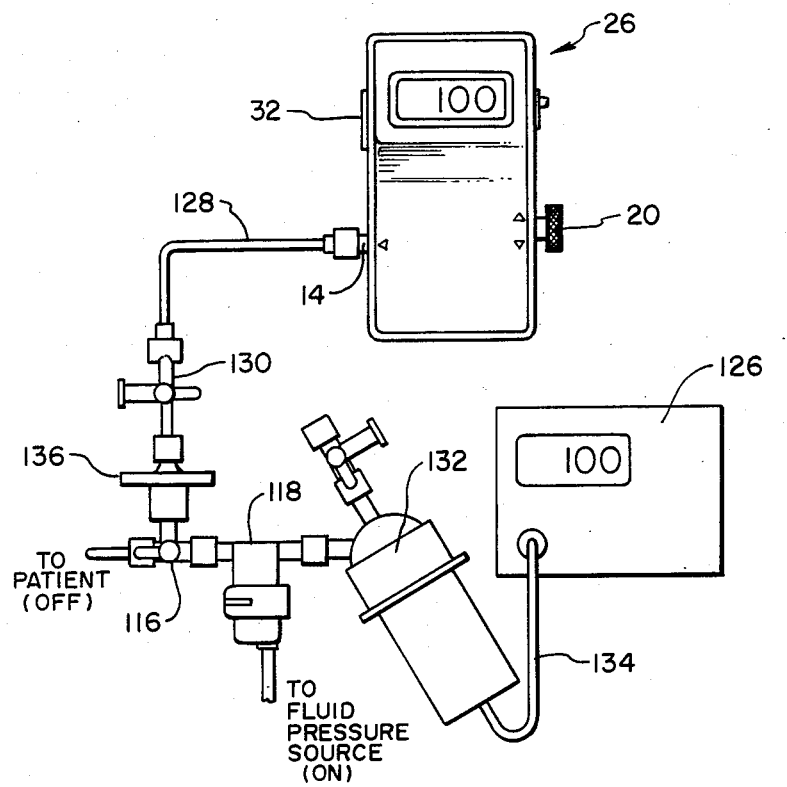
FIG. 12 is a diagram illustrating the use of the device shown in FIG. 2 to verify the calibration of a conventional pressure transducer in a direct blood pressure monitoring system.
Figure 13:
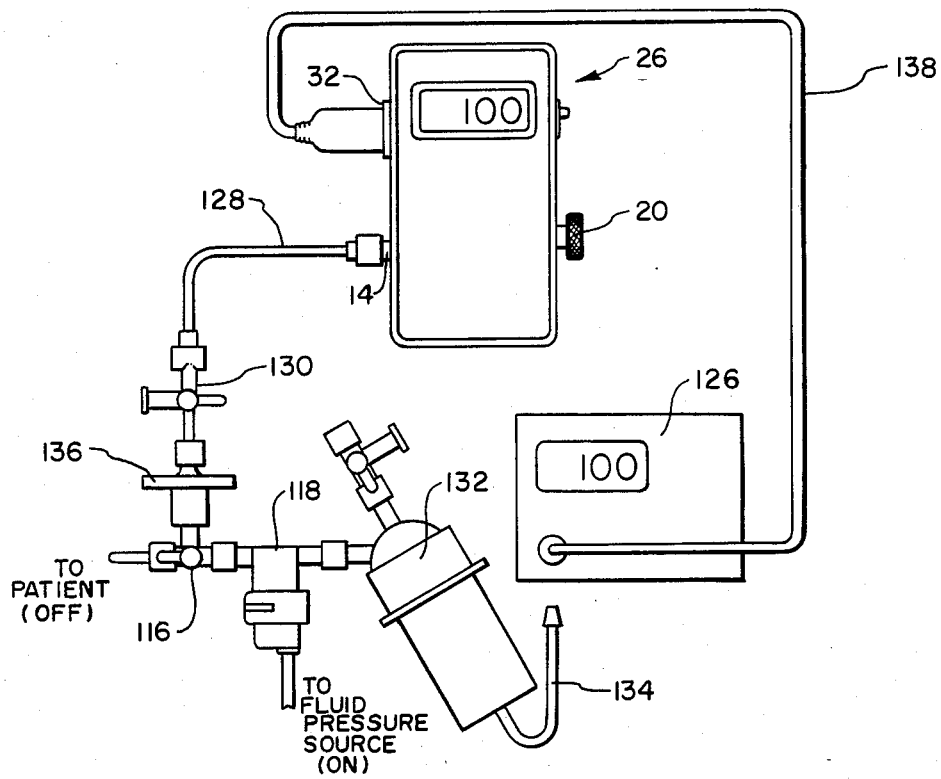
FIG. 13 is a diagram illustrating the use of the device shown in FIG. 2 to bypass the transducer of the system shown in FIG. 12.

Use of device 26 with a direct blood pressure monitoring system employing a nondisposable or semidisposable pressure transducer, is illustrated in FIGS. 12 and 13. There, nondisposable or semidisposable pressure transducer 132 is coupled through stopcock 116 to a fluid filled catheter inserted within a circulatory vessel of a patient as before. The sterile coupling fluid is provided to nondisposable or semidisposable transducer 132 and to the catheter through a continuous flush device 118, similar in all significant respects to that shown in FIGS. 10 and 11. The electrical output of nondisposable or semidisposable pressure transducer 132 is communicated through a monitor cable 134 to monitor 126.

In order to verify the calibration of nondisposable or semidisposable pressure transducer 132 using device 26, interconnections are effected as shown in FIG. 12. Hose 128 with optional cutoff valve 130 therein is connected through a sterile filter 136 to stopcock 116 on the sterile side of nondisposable or semidisposable pressure transducer 132. A positive pressure, as shown for example in FIG. 12 to be 100 mmHg, is generated in device 26 and applied to nondisposable or semidisposable pressure transducer 132. Stopcock 116, being closed in the direction of the patient, permits application of this positive pressure to the sterile side of nondisposable or semidisposable transducer 132. As a result, a readable output is electronically derived from nondisposable or semidisposable pressure transducer 132 for display on monitor 126. This may be checked against that on device 26 to verify the calibration of the pressure monitoring system.

If the calibration of nondisposable or semidisposable pressure transducer 132 cannot be verified, then the source of malfunction in the system must be located. This is accomplished, as it was in the case illustrated in FIG. 11, by applying the electrical output signal appearing at electrical connector 32 of device 26 from the substitute transducer therein to selected electrical locations in the monitoring system in order to determine the location of the malfunction. As shown in FIG. 13, a cable 138 has been inserted into electrical connector 32 of device 26 and directly to monitor 126. A pressure of 100 mmHg has been generated in device 26. A reading of an equal pressure on monitor 126, as shown in FIG. 13, indicates that monitor 126 is functioning correctly and that the source of malfunction is in nondisposable or semidisposable pressure transducer 132 or in monitor cable 134. Again, if disconnection of hose 128 either at output port 14 or at sterile filter 136 is required, it is also necessary to take appropriate steps to prevent the output pressure appearing at output port 14 from venting to atmosphere.

The method and apparatus described above provides the user of a direct blood pressure monitoring system with a simple and reliable means of verifying the accuracy and calibration of the entire monitoring system. A device such as device 26 offers the additional advantage of being usable to determine the source of any pressure monitoring system malfunction by replacing the on-line transducer of the pressure monitoring system. As applied to a system employing a disposable pressure transducer, such as a disposable pressure transducer 114 shown in FIGS. 10 and 11, this entire system check can be done without breaking into the sterile side of the on-line transducer. Device 26 is portable, hand held, and battery operated, rendering verification of calibration simple and eliminating the need for independent testing devices, such as transducer simulators, sphygmomanometers, fluid manometers and the like.

The invention may be embodied in other specific forms without departing from its spirit or other essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a pressure monitoring system having an on-line pressure transducer and a monitor for displaying an operator readable output electronically derived from said on-line pressure transducer, a device for selectively calibrating said on-line pressure transducer from known test pressures and for selectively bypassing said on-line pressure transducer to isolate defective electrical components of said pressure monitoring system, said device comprising:
   (a) operator-variable means for generating a known test pressure;
   (b) pressure calibration means coupled to said known test pressure for displaying on said device a calibrated output indicating the level of said known test pressure;
   (c) bypass means for transforming said known test pressure into an electrical output signal of the type derived from said on-line pressure transducer in said monitoring system, said output signal corresponding to the level of said known test pressure;
   (d) first output means selectively couplable to said monitoring system for applying said known test pressure to said on-line pressure transducer to produce on said monitor a first operator readable output so that said first operator readable output on said monitor can be checked against said calibrated output on said device when calibrating said monitoring system; and
   (e) second output means selectively couplable to said monitoring system for electrically bypassing said on-line pressure transducer with said bypass means, said output signal of said bypass means producing on said monitor a second operator readable output so that said second operator readable output on said monitor can be checked against said calibrated output on said device to isolate defective electrical components of said pressure monitoring system.

2. A device as recited in claim 1, wherein said operator-variable means comprises a manually operable pressure cylinder.

3. A device as recited in claim 2, wherein said pressure cylinder comprises means for generating both positive and negative pressures.

4. A device as recited in claim 1 wherein said pressure calibration means comprises:

(a) a precision pressure transducer coupled to said known test pressure for producing said electrical output signal corresponding to the level of said known test pressure;
   (b) a test pressure level display panel; and
   (c) an electronic circuit for receiving said electrical output signal from said precision pressure transducer and driving said test pressure level display panel to display said calibrated output indicating the level of said known test pressure.

5. A device as recited in claim 1, wherein said pressure calibration means is battery operated.

6. A device as recited in claim 1 wherein said bypass means comprises:
   (a) a dielectric substrate having first and second sides and an aperture therebetween, said first side being coupled at said aperture to said known test pressure;
   (b) a substitute pressure transducer supported on said second side of said dielectric substrate referenced to atmospheric pressure; and
   (c) electrical connections coupling said substitute pressure transducer to said second output means.

7. A device as recited in claim 6, wherein said substitute pressure transducer comprises:
   (a) a semiconductor pressure diaphragm sealed at the periphery thereof on said second side of said dielectric substrate over said aperture therein;
   (b) a piezoresistive strain gauge formed on said diaphragm on the side thereof opposite said aperture; and
   (c) a temperature compensation circuit on said second side of said dielectric substrate electrically connected to said piezoresistive strain gauge.

8. A device as recited in claim 7, wherein said strain gauge and said temperature compensation circuit of said substitute pressure transducer are substantially identical to any strain gauge and temperature compensation circuit employed in said on-line pressure transducer in said pressure monitoring system.

9. A device as recited in claim 6, wherein said substitute pressure transducer is powered by said pressure monitoring system through said second output means when said second output means is electrically coupled to said pressure monitoring system.

10. A device as recited in claim 1, wherein said device is dimensioned so as to be held in the hand of an operator.

11. In a direct blood pressure monitoring system having an on-line pressure transducer referenced at a first side thereof to atmospheric pressure and coupled at a second side thereof through a fluid in a catheter adapted to be inserted into a circulatory vessel of a patient, and having a monitor for displaying an operator readable output electronically derived from said on-line pressure transducer, a device for selectively calibrating said on-line pressure transducer from known test pressures and for selectively bypassing said on-line pressure transducer to isolate defective electrical components of said pressure monitoring system, said device comprising:
   (a) a manually operable pressure cylinder that generates a known test pressure;
   (b) pressure calibration means coupled to said known test pressure for displaying on said device a calibrated output indicating the level of said known test pressure;

(c) a substitute pressure transducer coupled to said known test pressure and referenced to atmospheric pressure that transforms said known test pressure into an electrical output signal of the type derived from said on-line pressure transducer in said monitoring system, said output signal corresponding to the level of said known test pressure;

(d) a closeable output port connected to said pressure cylinder that selectively couples to said monitoring system to apply said known test pressure to said on-line pressure transducer in said monitoring system and to produce on said monitor thereof a first operator readable output, said first operator readable output reflective of the responsiveness of said monitoring system, inclusive of said on-line pressure transducer, to said known test pressure, so that said first operator readable output on said monitor can be checked against said calibrated output on said device in calibrating said monitoring system; and (e) an electrical receptacle connected to said substitute pressure transducer, said electrical receptacle capable of receiving a cooperating electrical plug at one end of a connection cable, the other end of said connection cable couplable electrically to said monitoring system so as to bypass said on-line pressure transducer with said substitute pressure transducer, said output signal of said substitute transducer producing on said monitor a second operator readable output reflective of the electrical responsiveness of said pressure monitoring system with said on-line pressure transducer thereof removed, so that said second operator readable output on said monitor can be checked against said calibrated output on said device to isolate defective electrical components of said pressure monitoring system.

12. A device as recited in claim 11, wherein said pressure cylinder comprises means for generating both positive and negative pressures, such that by selecting an appropriate test pressure within said range, said output port on said pressure cylinder can be coupled to either said first or said second side of said on-line pressure transducer for calibrating said monitoring system.

13. A device as recited in claim 11, wherein said pressure calibration means comprises:

(a) a precision pressure transducer coupled to said known test pressure that produces said electrical output signal corresponding to the level of said known test pressure;

(b) a test pressure level display panel; and (c) an electronic circuit for receiving said electrical output signal from said precision transducer and driving said test pressure level display panel to display said calibrated output indicating the level of said known test pressure in operator-readable form.

14. A device as recited in claim 11, wherein said pressure calibration means is battery operated.

15. A device as recited in claim 11, wherein said substitute pressure transducer is powered by said pressure monitoring system through said electrical receptacle when said electrical receptacle is coupled through said connector cable to said monitoring system.

16. A device as recited in claim 11, wherein said substitute pressure transducer comprises:

(a) a semiconductor pressure diaphragm having a first side thereof coupled to said known test pressure and having a second side thereof referenced to atmospheric pressure;

(b) a piezoresistive strain gauge formed on said diaphragm on the side thereof referenced to atmospheric pressure; and (c) a temperature-compensation circuit connected to said piezoresistive strain gauge.

17. A device as recited in claim 16, wherein said strain gauge and said temperature compensation circuit of said substitute transducer are substantially similar to any strain gauge and temperature compensation circuit employed in said on-line pressure transducer in said pressure monitoring system.

18. A device as recited in claim 17, wherein said device is dimensioned so as to be held in the hand of an operator.

19. In a pressure monitoring system having an on-line pressure transducer and a monitor for displaying an operator readable output electronically derived from said on-line pressure transducer, a device for selectively bypassing said on-line pressure transducer to isolate defective electrical components of said pressure monitoring system, said device comprising:

(a) operator variable means for generating a known test pressure;

(b) pressure calibration means coupled to said known test pressure for displaying on said device a calibrated output indicative of said known test pressure;

(c) bypass means for transforming said known test pressure into an electrical output signal of the type derived from said on-line pressure transducer in said monitoring system, said bypass means being capable of producing electrical output signals within a continuous range of values and said output signal corresponding to the level of said known test pressure; and (d) an electrical receptacle connected to said bypass means for receiving therein a cooperating electrical plug at one end of a connection cable, the other end of said connection cable couplable electrically to said monitoring system to replace with said output signal from said bypass means, said on-line pressure transducer as the source of operator readable output to said monitoring system, said output signal of said bypass means producing on said monitor an operator readable output reflective of the electrical responsiveness of said pressure monitoring system with said on-line pressure transducer thereof removed, so that said operator readable output on said monitor can be checked against said calibrated output on said device to isolate defective electrical components of said pressure monitoring system.

20. A device as recited in claim 19, wherein said means for generating said known test pressure comprises a manually operable pressure cylinder.

21. A device as recited in claim 19, wherein said pressure cylinder comprises means for generating both positive and negative pressures.

22. A device as recited in claim 19, wherein said bypass means comprises a substitute pressure transducer substantially identical to said on-line pressure transducer in said pressure monitoring system.

23. In a pressure monitoring system having an on-line pressure transducer and a monitor for displaying an operator readable output electronically derived from said on-line pressure transducer, a method for selectively calibrating said on-line pressure transducer from known test pressures and for selectively bypassing said on-line pressure transducer to isolate defective electrical components of said pressure monitoring system, said method comprising the steps of:

(a) generating a known test pressure;
(b) applying said known test pressure simultaneously to a pressure calibration means for displaying a calibrated output indicating the level of said known test pressure and to a substitute pressure transducer referenced to atmospheric pressure for transforming said known test pressure into an electrical output signal of the type derived from said on-line pressure transducer and said monitoring system, said output signal corresponding to the level of said known test pressure;
(c) selectively coupling said known test pressure to said on-line pressure transducer in said monitoring system to produce on said monitor thereof a first operator readable output, said first operator readable output reflective of the responsiveness of said monitoring system, inclusive of said on-line pressure transducer, to said known test pressure;
(d) checking said first operator readable output on said monitor against said calibrated output on said device to calibrate said monitoring system;
(e) selectively connecting said output signal of said substitute transducer to said monitoring system to replace said on-line pressure transducer with said substitute transducer as the source of said operator readable output to said monitoring system, said output signal of said substitute transducer producing on said monitor a second operator readable output reflective of the electrical responsiveness of said pressure monitoring system with said on-line pressure transducer thereof removed; and
(f) checking said second operator readable output on said monitor against said calibrated output to isolate defective electrical components of said pressure monitoring system.

24. A method as recited in claim 23, wherein said step of connecting said output signal of said substitute transducer to said monitoring system comprises the steps of disconnecting said on-line transducer from said pressure monitoring system, and precluding said known test pressure from being vented to atmosphere.

25. A method a recited in claim 23, wherein said step of generating a known test pressure comprises the step of generating said known test pressure with a manually operable pressure cylinder.

26. A method as recited in claim 25, wherein said pressure monitoring system comprises a direct blood pressure monitoring system, wherein said on-line pressure transducer is referenced at a first side thereof to atmospheric pressure and is coupled at a second side thereof through a fluid in a catheter inserted into a circulatory vessel of a patient, and wherein said method further comprises the step of selectively coupling said known test pressure to said first or said second said on-line pressure transducer depending upon whether a positive or negative known test pressure is generated by said pressure cylinder.

27. A method as recited in claim 23, wherein said step of generating a known test pressure comprises the step of generating said known test pressure with a manually operable pressure cylinder capable of generating test pressures within a range of test pressures that includes both positive and negative pressures.

28. A method as recited in claim 23, wherein said step of applying said known test pressure simultaneously to a pressure calibration means and to a substitute pressure transducer comprises the step of applying said known test pressure to a substitute transducer substantially identical to said on-line transducer in said monitoring system.

29. A method as recited in claim 23, wherein an additional known test pressure is generated before said step of checking said second operator readable output against said calibrated output.

30. In a pressure monitoring system having an on-line pressure transducer and a monitor for displaying an operator readable output electronically derived from said on-line pressure transducer, a device for selectively bypassing said on-line pressure transducer to isolate defective electrical components of said pressure monitoring system, said device comprising:

(a) a manually operable pressure cylinder that generates a known test pressure;
(b) pressure calibration means coupled to said known test pressure for displaying on said device a calibrated output indicating the level of said known test pressure;
(c) a substitute pressure transducer coupled to said known test pressure and referenced to atmospheric pressure that transforms said known test pressure into an electrical output signal of the type derived from said on-line pressure transducer in said monitoring system, said substitute pressure transducer being capable of producing electrical output signals within a continuous range of values and said output signal corresponding to the level of said known test pressure; and
(d) an electrical receptacle connected to said substitute pressure transducer, said electrical receptacle capable of receiving a cooperating electrical plug at one end of a connection cable, the other end of said connection cable couplable electrically to said monitoring system so as to bypass said on-line pressure transducer with said substitute pressure transducer, said output signal of said substitute transducer producing on said monitor an operator readable output reflective of the electrical responsiveness of said pressure monitoring system with said on-line pressure transducer thereof removed, so that said operator readable output on said monitor can be checked against said calibrated output on said device to isolate defective electrical components of said pressure monitoring system.

* * * * *

UNITED STATES PATENT AND TRADEMARK OFFICE
CERTIFICATE OF CORRECTION

PATENT NO. : 4,658,829

DATED : April 21, 1987

INVENTOR(S) : William D. Wallace

It is certified that error appears in the above-identified patent and that said Letters Patent is hereby corrected as shown below:

Column 4, line 37, "is" should be --its--

Signed and Sealed this

Twenty-fifth Day of August, 1987

Attest:

DONALD J. QUIGG

*Attesting Officer*         *Commissioner of Patents and Trademarks*